(12) United States Patent
Tanaka

(10) Patent No.: US 8,778,388 B2
(45) Date of Patent: Jul. 15, 2014

(54) ACIDIC CARRAGEENAN COMPOSITION FOR EXTERNAL USE

(75) Inventor: Masaya Tanaka, Kobe (JP)

(73) Assignee: Neochemir Inc., Kobe-shi (JP)

( * ) Notice: Subject to any disclaimer, the term of this patent is extended or adjusted under 35 U.S.C. 154(b) by 223 days.

(21) Appl. No.: 13/409,415

(22) Filed: Mar. 1, 2012

(65) Prior Publication Data

US 2012/0165291 A1 Jun. 28, 2012

Related U.S. Application Data

(63) Continuation of application No. 10/479,210, filed as application No. PCT/JP02/05402 on May 31, 2002, now Pat. No. 8,153,143.

(30) Foreign Application Priority Data

Jun. 1, 2001 (JP) ................................. 2001-166901
Oct. 24, 2011 (JP) ................................. 2001-326552

(51) Int. Cl.
*A61F 13/02* (2006.01)
*A61K 9/70* (2006.01)

(52) U.S. Cl.
USPC ........................................................ 424/449

(58) Field of Classification Search
CPC ............. A61Q 1/02; A61Q 1/12; A61Q 1/14; C08L 1/00; C08B 37/00
See application file for complete search history.

(56) References Cited

U.S. PATENT DOCUMENTS

| | | | |
|---|---|---|---|
| 4,666,707 A | 5/1987 | Eguchi et al. | |
| 4,866,707 A * | 9/1989 | Marshall et al. | 714/749 |
| 4,935,228 A | 6/1990 | Finkenaur et al. | |
| 4,935,229 A | 6/1990 | Naito et al. | |
| 5,219,562 A | 6/1993 | Fujiu et al. | |
| 5,288,479 A | 2/1994 | Gorman et al. | |
| 5,961,999 A | 10/1999 | Bimczok et al. | |
| 6,010,706 A | 1/2000 | Candau et al. | |
| 6,482,826 B1 | 11/2002 | Pierard | |
| 2003/0074743 A1 | 4/2003 | Noguchi et al. | |
| 2003/0148931 A1 | 8/2003 | Takahashi et al. | |

FOREIGN PATENT DOCUMENTS

| | | |
|---|---|---|
| DE | 831096 C | 2/1952 |
| EP | 0174840 B1 | 8/1990 |
| EP | 0679387 A1 | 11/1995 |
| EP | 0750904 A1 | 1/1997 |
| EP | 1110971 A1 | 6/2001 |
| EP | 1138308 A2 | 10/2001 |
| GB | 1372382 A | 10/1974 |
| GB | 2182339 A | 5/1987 |
| JP | 05-058881 A | 3/1993 |
| JP | 05-117131 A | 5/1993 |
| JP | 05-170625 A | 7/1993 |
| JP | 5-178718 A | 7/1993 |
| JP | 06-345628 A | 12/1994 |
| JP | 07-010720 A | 1/1995 |
| JP | 07-277994 A | 10/1995 |
| JP | 8-1142 A | 1/1996 |
| JP | 08-092060 A | 4/1996 |
| JP | 08-283138 A | 10/1996 |
| JP | 09-077628 A | 3/1997 |
| JP | 09-194322 A | 7/1997 |
| JP | 09-227387 A | 9/1997 |
| JP | 09-278629 A | 10/1997 |
| JP | 09-295918 A | 11/1997 |
| JP | 9-315925 A | 12/1997 |
| JP | 10-17457 A | 1/1998 |
| JP | 11-209292 A | 8/1999 |
| JP | 2000-169322 A | 6/2000 |
| JP | 2000-178142 A | 6/2000 |
| JP | 2000-239122 A | 9/2000 |
| JP | 2000-281548 A | 10/2000 |
| JP | 2001-064152 A | 3/2001 |
| JP | 2002-080330 A | 3/2002 |
| JP | 2002-097125 A | 4/2002 |
| JP | 2002-332248 A | 11/2002 |
| JP | 2002-332249 A | 11/2002 |
| JP | 2002-332279 A | 11/2002 |
| WO | 97-45510 A1 | 12/1997 |
| WO | 99-07347 A1 | 2/1999 |
| WO | 02-15878 A1 | 2/2002 |

OTHER PUBLICATIONS

Japanese Office Action dated Aug. 28, 2012, issued in corresponding Japanese patent application No. 2009-100892.
Internationl Search Report of PCT/JP02/05402, date of mailing Aug. 20, 2002.
Japanese Office Action dated Feb. 17, 2009, issued in corresponding Japanese Patent Application No. 2003-501414.
Japanese Office Action dated Jul. 7, 2009, issued in corresponding Japanese Patent Application No. 2003-501414.
Supplementary European Search Report dated Aug. 25, 2005, issued in corresponding European Patent Application No. 02733271.

\* cited by examiner

*Primary Examiner* — Carlos Azpuru
(74) *Attorney, Agent, or Firm* — Westerman, Hattori, Daniels & Adrian, LLP

(57) ABSTRACT

An acidic composition for external use which contains an acidic polysaccharide and water as essential ingredients, and an agent for accelerating the penetration into skin or the like of a cosmetic preparation, hair-growing agent or preparation for external use, each containing the composition. The composition is easy to manufacture, and shows a stronger cosmetic or therapeutic effects than conventional compositions.

7 Claims, No Drawings

ACIDIC CARRAGEENAN COMPOSITION FOR EXTERNAL USE

CROSS REFERENCE TO RELATED APPLICATIONS

This U.S. patent application claims priority as a continuation application from co-pending U.S. non-provisional application Ser. No. 10/479,210, filed Dec. 1, 2003, which is a 371 U.S. National Stage application of PCT/JP02/05402, filed May 31, 2002, the subject matter being incorporated herein by reference in its entirety.

TECHNICAL FIELD

The present invention relates to an acidic composition for external use which has cosmetic effects, a hair-growing effect, and an effect in accelerating penetration into skin or the like of preparations for external use such as drugs, cosmetic preparations, and relates to an agent for accelerating penetration into skin or the like of a cosmetic preparation, a hair-growing agent and a preparation for external use each containing the composition.

BACKGROUND ART

Acidic polysaccharides are known to show diverse forms of physiological activity such as an effect in impeding coagulation of the blood, an effect in controlling the activity of cell proliferation factors, an effect in hindering the adhesion of viruses to cells, an anti-inflammatory effect, an immunological activating effect, an anti-cancer effect, a hemostatic effect and the like, and these compounds may be expected to have various effects as active ingredients in drugs and cosmetics. However, the use of such compounds in preparations for external use is rare, and the effects of these compounds in the case of such use are insufficient. As examples of cosmetic preparations, a pore shrinking agent containing a sulfated polysaccharide as an active ingredient, and a cosmetic preparation for suppressing the prominence of pores that contains this pore shrinking agent, have been proposed in Japanese Patent Application Laid-Open No. 2000-169322; however, the effects of these preparations are insufficient.

In regard to hair-growing agents, for example, a hair-nurturing agent containing a de-cationized acidic polysaccharide obtained from an acidic polysaccharide as an active ingredient is disclosed in Japanese Patent No. 2583812. However, the effect of this agent is insufficient, and since the metal cations of the acidic polysaccharide are converted into hydrogen ions using a cationic ion exchange resin in the manufacturing process, the amount of the agent that can be manufactured is limited, and considerable time and expense are required in order to manufacture this agent.

In light of such conditions, it is an object of the present invention to provide an acidic polysaccharide composition for external use which is easy to manufacture, and which has stronger cosmetic effects, hair-growing effect or therapeutic effect than other novel or universally known compositions.

DISCLOSURE OF THE INVENTION

The present inventor discovered that an acidic composition for external use containing acidic polysaccharides and water as essential ingredients has (1) cosmetic effects in making hair smooth and supple, adjusting the texture of skin, increasing the tension of skin, stretching out wrinkles, whitening skin, imparting an impression of transparency and moistened feeling to skin, lightening spots and making pores less noticeable, (2) a hair-growing effect in suppressing hair-loss and promoting growth of hair, and (3) a penetration accelerating effect in accelerating penetration of preparations for external use, such as drugs, cosmetics or the like, into skin or the like. This discovery led to the perfection of the present invention. Furthermore, the term "skin or the like" as used in the present invention refers to tissues of epithelial cell origin such as skin, mucous membranes, hair, nails and the like.

The acidic polysaccharides used in the acidic composition for external use provided by the present invention may appropriately comprise one or more polysaccharides selected from a group comprising sulfated polysaccharides that have sulfuric acid groups in the molecule, and acidic polysaccharides that have carboxyl groups in the molecule (hereafter referred to as "carboxyl polysaccharides"). Furthermore, because of problems in terms of solubility and the like, acidic polysaccharides are ordinarily used as salts of alkali metals such as sodium, potassium or the like, or salts of alkaline earth metals such as calcium or the like; in the present invention, acidic polysaccharides include such salts unless otherwise specifically noted.

One or more sulfated polysaccharides selected from a group comprising natural sulfated polysaccharides and semi-synthetic sulfated polysaccharides obtained by converting neutral polysaccharides or natural sulfated polysaccharides using a sulfating reagent or the like may be used as sulfated polysaccharides; however, the present invention is not particularly limited to such polysaccharides. Concrete examples of such sulfated polysaccharides include carrageenan, keratan sulfate, chondroitin sulfate, dextran sulfate, dermatan sulfate, fucoidan, funoran, heparin, porphyran and the like. One or more of these polysaccharides may be used. Of course, one or more compounds selected from the above-mentioned group comprising alkali metal salts of sulfated polysaccharides such as sodium salts, potassium salts and the like, and alkaline earth metals salts of sulfated polysaccharides such as calcium salts and the like, may also be used. Among these substances, carrageenan has protein reactivity and a high affinity for tissues such as skin or the like, and is therefore especially desirable.

One or more carboxyl polysaccharides selected from a group comprising natural carboxyl polysaccharides and semi-synthetic carboxyl polysaccharides obtained by carboxylating neutral polysaccharides or natural polysaccharides using a carboxylating reagent or the like may be used as carboxyl polysaccharides; however, the present invention is not particularly limited to such polysaccharides. Concrete examples of such compounds include alginic acid, karaya gum, carboxymethylcellulose, carboxyethylcellulose, carboxymethylethylcellulose, carboxymethyldextran, carboxymethyl starch, gellan gum, hyaluronic acid, pectin and the like. One or more of these compounds may be used. Of course, one or more compounds selected from the above-mentioned group comprising alkali-metal salts of carboxyl polysaccharides such as sodium salts, potassium salts and the like, and alkaline earth metals salts of carboxyl polysaccharides such as calcium salts and the like, may also be used. Among these compounds, alginic acid, hyaluronic acid and pectin also have moisture retaining properties and the like, and are therefore desirable, and alginic acid is superior in terms of use characteristics and the like, and is therefore especially desirable.

The amount of acidic polysaccharides mixed with the acidic composition for external use provided by the present invention is preferably 0.001 to 5 wt %; and even more-preferably 0.01 to 3 wt %, relative to the total amount of the composition. If the amount that is mixed is less than 0.001 wt %, no cosmetic effect, hair-growing effect or effect in accelerating the penetration of preparations for external use into skin or the like can be expected. On the other hand, even if the amount mixed exceeds 5 wt %, no additional effect can be expected. It is known that acidic polysaccharides show an effect in impeding coagulation of the blood, an effect in controlling the activity of cell proliferation factors, an effect in hindering the adhesion of viruses to cells, an anti-inflammatory effect, an immunological activating effect, an anti-cancer effect, a hemostatic effect and the like; in all cases, such activity is shown in the vicinity of a pH of 7, which is more or less the same as the pH of body fluids. However, the fact that acidic polysaccharides show (1) cosmetic effects in making hair smooth and supple, adjusting the texture of skin, increasing the tension of skin, stretching out wrinkles, whitening skin, imparting an impression of transparency and moistened feeling to skin, lightening spots and making pores less noticeable, (2) a hair-growing effect in suppressing hair-loss and promoting growth of hair, and (3) an penetration accelerating effect in accelerating penetration of preparations for external use such as drugs, cosmetics or the like into skin or the like, when such acidic polysaccharides are applied to skin or the like as an acidic composition for external use has been completely unknown in the past. Furthermore, if the acidic composition for external use provided by the present invention is administered by a method other than external application, such as oral administration, injection or the like, the acidic polysaccharides cannot act under acidic conditions in desired organs, tissues or the like because of the buffering action of body fluids and the like, so that the effect of the present invention is not obtained.

Since acidic polysaccharides hardly dissolve when used "as is", these polysaccharides are ordinarily used in the form of salts; when dissolved in water, the resulted solutions are roughly neutral to weakly alkaline. The acidic composition for external use provided by the present invention can be made into an acidic solution using an acid or acidic electrolyzed water. For example, in cases where an acid is used, manufacture can easily be accomplished by mixing the acid (s) and water with the acidic polysaccharide(s) avoiding decomposition or the like of the acidic polysaccharide(s) by the acid(s). Natural water, tap water, or purified water such as ion exchanged water, membrane-filtered water, distilled water or the like can be used without any particular restrictions as the above-mentioned water. However, if water in which clusters (aggregations of water molecules) are decreased in size by using irradiation with electromagnetic waves such as high-frequency waves, far infrared radiation or the like, exposure to ultrasound, application of a voltage, electrolysis, high-speed rotation of the water or the like is used, not only can the dissolution of the acidic polysaccharides be promoted, but the penetration and absorption of the prepared acidic composition for external use into skin or the like can be accelerated; accordingly, such water is more desirable.

One or more acids selected from a group comprising inorganic acids and organic acids may be used as the above-mentioned acid; there are no particular restrictions on the acid used. Examples of inorganic acids that can be used include sulfuric acid, hydrochloric acid, nitric acid, sulfamic acid, phosphoric acid, potassium dihydrogenphosphate, sodium dihydrogenphosphate, sodium pyrosulfite, potassium pyrosulfite, sodium sulfite, potassium sulfite, acidic sodium hexametaphosphate, acidic potassium hexametaphosphate, acidic sodium pyrophosphate, acidic potassium pyrophosphate and the like. One or more of these acids may be used.

Examples of organic acids that can be used include linear fatty acids such as formic acid, acetic acid, propionic acid, butyric acid, valeric acid and the like, dicarboxylic acids such as oxalic acid, malonic acid, succinic acid, glutaric acid, adipic acid, pimelic acid, fumaric acid, maleic acid, phthalic acid, isophthalic acid, terephthalic acid and the like, acidic amino acids such as glutamic acid, aspartic acid and the like, and oxy acids such as glycolic acid, malic acid, tartaric acid, citric acid, lactic acid, hydroxyacrylic acid, α-oxybutyric acid, glyceric acid, tartronic acid, salicylic acid, gallic acid, tropic acid, ascorbic acid, gluconic acid and the like. One or more of these acids may be used.

Acidic electrolyzed water manufactured by a universally known method can be used as the above-mentioned acidic electrolyzed water. For example, in the case of a batch type electrolyzed water manufacturing apparatus, acidic water rich in hydrogen ions that are produced on the anode side can be used. In regard to the water used in the manufacture of such acidic electrolyzed water, purified water or tap water may be appropriately used in accordance with the application. However, in order to increase the electrolysis efficiency of the water, it is desirable to perform electrolysis with an electrolyte such as sodium chloride or the like added to the water. Since clusters (comprising aggregations of water molecules) are small in acidic electrolyzed water, dissolution of acidic polysaccharides is easy, and the power of penetration into skin or the like is increased compared to cases in which the prepared composition for external use is manufactured using an acid and ordinary water, so that the cosmetic effects, hair-growing effect and effect in accelerating the penetration into skin or the like of preparations for external use such as drugs for external use, cosmetic preparations or the like, are strengthened. Furthermore, since acidic electrolyzed water is superior in terms of microbicidal and virucidal effects, a microbicidal action can be performed at the same time that the acidic composition for external use is prepared.

Accordingly, not only is this convenient, but there is no need to mix preservatives, microbicidal agents or the like, that might possibly damage skin or mucous membranes, with the composition. An acid or alkali may be used together with acidic electrolyzed water for purposes of pH adjustment or the like; there are no particular restrictions on an acid or an alkali used in this case.

It is sufficient if the pH of the acidic composition for external use provided by the present invention is acidic within a range that is such that the composition does not damage skin; a pH of 2.0 to 6.0 is desirable, and a pH of 2.5 to 5.0 is even more desirable. If the pH is lower than 2.0, the acidity is too strong, so that there is a danger of damage to skin or the like; on the other hand, if the pH exceeds 6.0, the effect of the present invention cannot be obtained. As long as the acidity of the composition for external use provided by the present invention is within the pH range of 2.0 to 6.0, the acidity of the composition can be adjusted to any desired acidity using an alkali such as sodium hydroxide or the like.

In addition to the above-mentioned essential components, raw materials ordinarily used in preparations for external use, e. g., alcohols, moisturizing agents, surfactants, thickeners, preservatives, oils, fragrances, coloring agents, ultraviolet absorbing/scattering agents, physiologically active substances and the like, may also be used in the acidic composition for external use provided by the present invention as long as they do not impair the effects of the present invention. Furthermore, the term "physiologically active substances and the like" as used in the present invention includes both substances used as drugs to treat or prevent diseases, and substances that have cosmetic effects such as whitening, amelioration of spots, amelioration of pigment deposition, stretching out of wrinkles and the like.

The acidic composition for external use provided by the present invention may be applied "as is" to skin or the like. However, as long as the composition is a preparation for external use, there are no particular restrictions on the agent type such as lotion, emulsion, gel, cream, plaster, spray, adhesive patch agent or the like. The composition itself shows a strong penetration into skin or the like. However, if the composition is mixed with another preparation for external use, the penetration into skin or the like of the preparation for external use that is thus mixed is reinforced; accordingly, especially in the case of preparations for external use that have a sticky feeling, this sticky feeling disappears in a short time when the agent is rubbed into skin or the like, so that a clean feeling is obtained, thus producing a desirable feeling of use. Furthermore, since there is no adhesion of the composition to clothing or the like following application, there is no soiling of clothing or the like, and in the case of drugs or the like for external use, the active ingredients or the like can be administered without waste. Accordingly, if the acidic composition for external use provided by the present invention is mixed with a preparation for external use such as a drug for external use, cosmetic preparation or the like and used as an agent for accelerating penetration into skin or the like, an effect comparable to that of the original preparation for external use can be obtained even if the dosage, number of times of administration, administration time or the like of preparation for external use is reduced.

The acidic composition for external use provided by the present invention can be more appropriately used as a hair-growing agent or cosmetic preparation by adding other raw materials. The hair-growing agent of the present invention can be manufactured by mixing the acidic composition for external use provided by the present invention as the active ingredient of a conventional hair-growing agent preparation. The amount that is mixed is preferably 0.001 to 5 wt %, and even more preferably 0.01 to 3 wt % (in terms of acidic polysaccharides), relative to the total amount of the hair-growing agent. The acidity is preferably pH 2.0 to 6.0, and is even more preferably pH 2.5 to 5.0. In cases where it is necessary to adjust the pH, the pH can be adjusted to the desired pH by adding an arbitrary acid or alkali. Other hair-growing substances and other physiologically active substances or the like may be mixed with the hair-growing agent of the present invention within limits as long as they do not impair the effects of the present invention. The hair-growing agent of the present invention can be used in the same manner as conventional hair-growing agents; it is sufficient if the hair-growing agent is rubbed into scalp once or more per day so that the hair-growing agent is uniformly spread over the entire scalp.

The cosmetic preparation of the present invention can be manufactured by mixing the acidic composition for external use provided by the present invention with a conventional cosmetic preparation composition; the amount that is mixed is preferably 0.001 to 5 wt %, and even more preferably 0.01 to 3 wt % (in terms of acidic polysaccharides), relative to the total amount of the cosmetic preparation. The acidity of the cosmetic preparation of the present invention is preferably pH 2.0 to 6.0, and is even more preferably pH 2.5 to 5.0. In cases where it is necessary to adjust the pH, the pH can be adjusted to the desired pH value by mixing an arbitrary acid or alkali with the composition. The cosmetic preparation of the present invention can be used in the same manner as a conventional cosmetic preparation; it is sufficient if an appropriate amount of this preparation is applied to desired area. The cosmetic preparation may be used once in order to obtain effects in making hair smooth and supple, adjusting the texture of skin, increasing the tension of skin, whitening skin, increasing a transparent impression of skin, or giving a moistened feeling to skin; however, the effects are greatly increased by using the preparation every day. In order to obtain effects in stretching out wrinkles, lightening spots, ameliorating pigment deposition or Making pores less prominent, it is desirable to use the preparation once or more per day for four days or longer.

The acidic composition for external use provided by the present invention can be mixed with a conventional preparation for external use as an agent that accelerates the penetration into skin or the like of drugs for external use, cosmetic preparations or the like. The amount of the composition that is mixed is preferably 0.001 to 5 wt %, and even more preferably 0.01 to 3 wt % (in terms of acidic polysaccharides), relative to the total amount of the preparation for external use. The acidity of the preparation for external use with which the composition is mixed is preferably pH 2.0 to 6.0, and is even more preferably pH 2.5 to 5.0. In cases where it is necessary to adjust the pH, the pH can be adjusted to the desired pH value by mixing an arbitrary acid or alkali with the composition. The preparation for external use with which the agent for accelerating penetration into skin or the like provided by the present invention is mixed can be used in the same manner as an conventional preparation for external use; since penetration into skin or the like is accelerated, an effect comparable to that of the original preparation for external use can be obtained even if the dosage, number of times of administration, administration time or the like of preparation for external use is reduced. Furthermore, in the case of a preparation for external use such as a physiologically active substance or the like, the amount that is mixed can be reduced as long as this substance is a physiologically active substance which does not suffer from problems such as modification, degeneration, loss of activity, a conspicuous drop in activity or the like as a result of acidity. Furthermore, if physiological substances or the like which do not suffer from problems such as modification, degeneration, loss of activity, a conspicuous drop in activity or the like as a result of acidity, but which could not be utilized in the past in preparations for external use because of a low transdermal absorption rate, are used as the above-mentioned preparations for external use with which the above-mentioned composition is mixed, the transdermal absorption rate of such agents is increased.

BEST MODE FOR CARRYING OUT THE INVENTION

Next, the present invention will be concretely described in terms of examples; however, the present invention is not limited to these examples.

Example 1

1.6 parts by weight of carrageenan was dispersed in 2 parts by weight of ethanol, and was then dissolved by gradually adding 200 parts by weight of distilled water, thus producing a somewhat viscous aqueous solution of carrageenan with a pH of 7.07. The acidity was then adjusted to a pH of 4.03 by adding dilute sulfuric acid with a pH of 0.77 to this aqueous solution, thus producing an acidic composition for external use.

Example 2

0.06 parts by weight of carrageenan was dispersed using 0.5 parts by weight of ethanol, and was then dissolved by gradually adding 25 parts by weight of distilled water, thus producing a somewhat viscous aqueous solution of carrageenan with a pH of 6.87. The acidity was adjusted to a pH of 4.10 by adding 0.1 N hydrochloric acid to this aqueous solution, and distilled water was further added to produce a total amount of 30 parts by weight, thus producing an acidic composition for external use with a pH of 4.17.

Example 3

0.24 parts by weight of carrageenan was dispersed using 0.5 parts by weight of ethanol, and was then dissolved by gradually adding 25 parts by weight of distilled water, thus producing a somewhat viscous aqueous solution of carrageenan with a pH of 6.76. The acidity was adjusted to a pH of 3.5 by adding 0.1 N nitric acid to this aqueous solution, and distilled water was further added to produce a total amount of 30 parts by weight, thus producing an acidic composition for external use with a pH of 3.54.

Example 4

0.24 parts by weight of carrageenan was dissolved in 30 parts by weight of distilled water. Then, 0.03 parts by weight of methylparaben was further dissolved, thus producing a somewhat viscous aqueous solution with a pH of 6.50. 1.5 parts by weight of sodium dihydrogenphosphate dihydrate was added to this aqueous solution and dissolved, thus producing an acid composition for external use with a pH of 4.45.

Example 5

0.24 parts by weight of carrageenan was dissolved in 30 parts by weight of water in which clusters (aggregations of water molecules) had been reduced in size by irradiation for 10 minutes with high-frequency waves from a microwave oven with an oscillation frequency of 2450 MHz. Then, 0.03 parts by weight of methylparaben was further added, thus producing a somewhat viscous aqueous solution with a pH of 7.11. 1.5 parts by weight of sodium dihydrogenphosphate was added to this aqueous solution and dissolved, thus producing an acidic composition for external use with a pH of 4.52.

Example 6

Hair-Growing Agent 6.25 parts by weight of the acidic composition for external use obtained in Example 1, 50.75 parts by weight of distilled water, 3 parts by weight of glycerol and 40 parts by weight of ethanol were mixed, thus producing 100 parts by weight of a liquid-form acidic composition for external use with a pH of 4.98, which had an acidic polysaccharide content of 0.05%.

Example 7

Aqueous Gel 4.2 parts by weight of a carboxyvinyl polymer and 0.2 parts by weight of methylparaben were swelled and dissolved with 200 parts by weight of distilled water, and this solution was allowed to stand overnight, thus producing a viscous liquid with a pH of 2.47. 7.5 parts by weight of the acidic composition for external use obtained in Example 3 was added to 30 parts by weight of this viscous liquid, and 3 parts by weight of a 2% aqueous solution of sodium hydroxide was further added, thus producing a gel-form acidic composition for external use with a pH of 4.25.

Example 8

Lotion 0.1 parts by weight of methylparaben was added to 100 parts by weight of distilled water and dissolved. Then 18 parts by weight of the acidic composition for external use obtained in Example 4 was further added, thus producing an acidic composition for external use with a pH of 4.46.

Example 9

Beauty Liquid

Purified water was added to 5.0 parts by weight of the acidic composition for external use obtained in Example 5, 0.95 parts by weight of sodium alginate, 0.095 parts by weight of methylparaben, 0.014 parts by weight of citric acid, 0.01 parts by weight of mulberry root extract, 0.01 parts by weight of perilla extract, 0.01 parts by weight of matricaria extract, 0.01 parts by weight of Saxifrage extract, and 0.01 parts by weight of rosemary extract to produce a total of 100 parts by weight, and these ingredients were dissolved, thus producing a somewhat viscous acidic composition for external use with a pH of 5.0.

Example 10

Anti-Inflammatory Preparation for External Use 0.2 parts by weight of the acidic composition for external Use obtained in Example 3 was added and mixed with 2.8 parts by weight of an ibuprofen piconol cream (commercial name Beshikamu, manufactured by Toni Yakuhin Kogyo K.K.), thus producing 3.0 parts by weight of a cream-form acidic composition for external use with a pH of 5.45.

Example 11

Milky Lotion 1 part by weight of the acidic composition for external use obtained in Example 1 was added and mixed with 19 parts by weight of a commercially marketed milky lotion (commercial name: Kanebo Exercise Body Up (Emulsion), R) manufactured by Kanebo, Ltd.), thus producing an emulsion-form acidic composition for external use with a pH of 5.85.

Example 12

Hair-Dyeing Assistant 5 parts by weight of the acidic composition for external use obtained in Example 3 was added and mixed with 45 parts by weight of a hydrogen peroxide cream agent (commercial name: Oxy-Cream F, manufactured by Takara Belmont Corp.), thus producing 50 parts by weight of a cream-form composition for external use with a pH of 4.70.

Example 13

0.25 parts by weight of sodium alginate was dissolved in 40 parts by weight of distilled water, thus producing a somewhat viscous aqueous solution of sodium alginate with a pH of 6.45. The acidity was adjusted to pH 4.51 by adding dilute sulfuric acid with a pH of 0.77 to this aqueous solution, and distilled water was further added to produce a total amount of 50 parts by weight, thus producing an acidic composition for external use with a pH of 4.54.

Example 14

0.25 parts by weight of sodium alginate was dissolved in 40 parts by weight of distilled water, thus producing a somewhat viscous aqueous solution of sodium alginate with a pH of 6.51. The acidity was adjusted to a pH of 4.11 by adding 0.1 N hydrochloric acid to this aqueous solution, and distilled water was further added to produce a total of 50 parts by weight, thus producing an acidic composition for external use with a pH of 4.13.

Example 15

0.25 parts by weight of sodium alginate was dissolved in 40 parts by weight of distilled water, thus producing a somewhat viscous aqueous solution of sodium alginate with a pH of 6.53. The acidity was adjusted to a pH of 3.86 by adding 0.1 N nitric acid to this aqueous solution, and distilled water was further added to produce a total of 50 parts by weight, thus producing an acidic composition for external use with a pH of 3.88.

Example 16

0.25 parts by weight of sodium alginate was dissolved in 50 parts by weight of distilled water, thus producing a somewhat viscous aqueous solution of sodium alginate with a pH of 6.51. 500 mg of sodium dihydrogenphosphate dihydrate was added to this aqueous solution, thus producing an acidic composition for external use with a pH of 4.62.

Example 17

0.25 parts by weight of sodium alginate was dissolved in 50 parts by weight of distilled water, thus producing a somewhat viscous aqueous solution of sodium alginate with a pH of 6.49. 0.4 parts by weight of potassium dihydrogenphosphate was added to this aqueous solution, thus producing an acidic composition for external use with a pH of 4.48.

The acidic compositions for external use provided by the present invention were evaluated as follows:

1. Test Relating to Effect in Whitening and Adjusting the Texture of Skin 19 female test subjects ranging in age from 29 to 41 years each rubbed 0.1 ml of one of the acidic compositions for external use obtained in Examples 1 through 11 and Examples 13 through 17 into the back of the left hand (with the compositions being applied by the test subjects themselves), and this back of the left hand was then compared with the back of the right hand, to which nothing had been applied. As a result, in all of the test subjects, according to an evaluation by a third party, the back of the left hand immediately showed a smooth white appearance, thus confirming an effect in whitening and adjusting the texture of skin. After one day or longer, each test subject similarly tested one of the acidic compositions for external use obtained in Examples 1 through 11 and Examples 13 through 17 that the test subject had not tried before; in this case, an effect in whitening and adjusting the texture of skin was observed in all of the acidic compositions for external use obtained in Examples 1 through 11 and Examples 13 through 17. The acidic compositions for external use obtained in Examples 1, 2 through 5, 7 and 9 showed a conspicuous effect, and the effect of the acidic composition for external use obtained in Example 5 was especially superior. All of the acidic compositions for external use used in this test penetrated into skin after being rubbed in only a few times by all of the test subjects.

2. Test of Amelioration of Pigment Deposition

Three female test subjects, who are 21, 22 and 23 years of age respectively and complained of pigment deposition in pimple scars, and in whom commercially marketed whitening cosmetics, internal agents showing an effect against pigment deposition or the like had no effect, applied an appropriate amount of the gel-form acidic composition for acidic use obtained in Example 7 to the areas of pigment deposition in the pimple scars twice a day on a daily basis. As a result, the 21- and 22-year-old test subjects showed an amelioration of pigment deposition in 5 days, and the 23-year-old test subject showed an amelioration of pigment deposition in 8 days, and the pigment deposition became hardly noticeable. Furthermore, in all of the test subjects, the acidic composition for external use obtained in Example 7 immediately penetrated into skin when rubbed in ten times or less, and there was no stickiness at all.

3. Test of Spot Amelioration

When six female test subjects ranging in age from 38 years to 61 years who complained of spots in the areas at the outside corners of the eyes and under the eyes were subjected to application of the acidic composition for external use obtained in Example 9 to the spots twice a day on a daily basis, in all of the test subjects lightening of these spots in two weeks, and in two of the test subjects a more or less complete disappearance of the spots were observed in the case of continuous use for three weeks or longer. Furthermore, in all of the test subjects, the acidic composition for external use obtained in Example 9 immediately penetrated into skin after being rubbed in only a few times, and there was no stickiness at all.

4. Test Relating to Effect in Imparting an Impression of Transparency to Skin and Adjusting the Texture of Skin Five female test subjects ranging in age from 29 years to 51 years were imaged with a CCD camera connected to a personal computer in order to produce 40× large photographs of the skin on both cheeks prior to the initiation of this test. Each test subject applied 0.3 ml of one of the acidic compositions for external use obtained in Example 1, 4, 8, 13 or 16 to the entire face twice a day (morning and evening) for 1 week. Then, on the eighth day, 40× large photographs of the skin on both cheeks were taken, and these photographs were compared with the earlier photographs. As a result, an impression of transparency of skin was recognized in all of the test subjects. Lines and bumps in skin were cleared up compared to the conditions prior to the initiation of the test, and an increase in the luster of skin surface was also confirmed. The effect of the acidic composition for external use obtained in Example 4 was especially conspicuous. All of the acidic compositions for external use used in this test showed immediate penetration into skin in all of the test subjects after being rubbed in only a few times, and there was no stickiness at all.

5. Test Relating to Effect in Increasing the Tension of Skin

Ten female test subjects ranging in age from 21 years to 37 years were subjected to application of 0.3 ml of one of the acidic compositions for external use obtained in Example 1 and Examples 2 through 9 to the entire face. As a result, all of the test subjects observed a feeling of tightening of skin and a so-called lift-up effect that raised the cheeks. At the same time, an effect that skin became whiter was observed in all of the test subjects. All of the acidic compositions for external use used in this test showed immediate penetration into skin in all of the test subjects after being rubbed in only a few times.

6. Test Relating to Effect of Making Pores Less Noticeable

Five female test subjects ranging in age from 22 years to 31 years, who were judged to have prominent pores in the nose according to both observations by third parties and reports from the test subjects themselves were subjected to application of 50 mg of the acidic composition for external use obtained in Example 2 to the right side of the nose, and 50 mg of a 1% sodium dextran sulfate lotion manufactured according to Example 2 of Japanese Patent Application Laid-Open No. 2000-169322, once a day for four days, all of the test subjects felt that the pores on the right side of the nose became less noticeable, and the pores on the right side of the nose were also judged to be less noticeable than the pores on the left side of the nose in observations made by third parties.

7. Test of Effect in Ameliorating Sticky Feeling of Cream (Acceleration of Penetration into Skin)

Six female test subjects ranging in age from 21 years to 23 years were subjected to application of 0.1 g of the emulsion-form acidic composition for external use obtained in Example 11 to the right hand, and 0.1 g of a IS commercially marketed milky lotion (commercial name: Kanebo Exercise Body Up (Emulsion), manufactured by Kanebo, Ltd.) to the left hand, and the feeling of stickiness when rubbed onto skin was compared. As a result, none of the test subjects felt any stickiness after rubbing in the emulsion-form acidic composition for external use of Example 11 twenty times or less. In contrast, in the case of the commercially marketed emulsion, a feeling of stickiness persisted even after the preparation was rubbed in more than 40 times. Furthermore, in all of the test subjects a conspicuous whitening effect on the right hand was observed.

8. Test Relating to Effect of Imparting Moistened Feeling to Skin

Two test subjects, i. e., a 7-year-old girl and a 12-year-old boy, swam for 1 hour in a warm-water pool. Afterward, when these test subjects respectively applied 0.2 g of the acidic composition for external use obtained in Example 4 to their faces, which had a dried-out stretched feeling, the composition was absorbed after being rubbed in only a few times, and the skin of the test subjects became moistened and smooth, with an effect that imparted moistened feeling to skin being observed.

9. Test of Hair-Growing Effect (1) Three male test subjects 33, 34 and 51 years of age, who suffered from hair loss with the underlying skin being somewhat visible through the hair, and who complained that no hair loss suppressing effect or hair-growing effect was obtained when a 0.05% de-cationized carrageenan lotion manufactured according to the composition example of hair-nourishing agent 2 of Example 3 of Japanese Patent No. 2583812 was used for one month, were subjected to application of the liquid-form acidic composition obtained in Example 6 to the entire scalp at the rate of 1 ml per administration, applied twice a day on a daily basis. As a result, within 7 days following the initiation of the test, a decrease in the number of hairs lost during washing of the hair to half or less of the number lost prior to the initiation of the test was seen in all of the test subjects, and the manifestation of a hair loss suppressing effect occurred very quickly. Furthermore, in the case of the 33-year-old test subject, the amount of hair increased with the underlying skin was no longer being noticeable in the second month of administration, and in the case of the 51-year-old test subject, a similar result was seen in the third month of administration. During this period, none of the test subjects showed any side effects.

10. Test of Effect in Accelerating the Penetration of Drugs into Skin

A 6-year-old female patient and a 7-year-old female patient suffering from atopic dermatitis with eczema on the insides of both elbows were subjected to application of 0.2 g of the cream-form acidic composition for external use obtained in Example 10 into the eczema on the inside of the right elbow by rubbing 30 times with fingers, and were [similarly] subjected to application of 0.2 g of an ibuprofen piconol cream (commercial name: Beshikamu, manufactured by Torii Yakuhin Kogyo K.K.) into the eczema on the inside of the left elbow by rubbing 30 times with fingers. After being rubbed in, the cream-form acidic composition for external use obtained in Example 10 had no sticky feeling; however, the ibuprofen piconol cream continued to have a sticky feeling. After 1 hour, both patients showed an improvement of the eczema on the inside of the right elbow to which the cream-form acidic composition for external use obtained in Example 10 was applied, with a reduction in redness. However, the inside of the left elbow to which the ibuprofen piconol cream was applied showed only a slight reduction in redness.

11. Test of Shortening of Hair Dyeing Time of Hair Dyeing Agent 5 g of a hair dyeing agent (commercial name: Top Model, manufactured by Takara Belmont Corp.) and 5 g of the cream-form acidic composition for external use obtained in Example 12 were mixed, and this mixture was used on the hair of a mannequin used for training in hair dyeing. As a result, hairy dyeing was accomplished in 10 minutes. The hair following this hair dyeing showed good luster compared to the hair prior to dyeing, and had a moist feeling. On the other hand, when 5 g of a hair dyeing agent (commercial name: Top Model, manufactured by Takara Belmont Corp.) and 5 g of a hydrogen peroxide cream agent (commercial name: Oxy-Cream F, manufactured by Takara Belmont Corp.) were mixed, and this mixture was used on the hair of a mannequin used for training in hair dyeing, a period of 40 minutes was required for the completion of the hair dyeing. The hair following this hair dyeing had a dry feeling compared to the hair prior to dyeing, and the luster was poor.

12. Test Relating to Effect of Making Hair Smooth and Supple

A 46-year-old male who complained that the hardness of his hair was bothersome was subjected to application of 1 g of the acidic composition for external use obtained in Example 16 by rubbing into his hair throughout. As a result, the hair of the test subject became extremely smooth and supple, and showed good luster.

Thus, the acidic compositions for external use provided by the present invention show cosmetic effects in making hair smooth and supple, adjusting the texture of skin, increasing the tension of skin, stretching out wrinkles, whitening skin, imparting an impression of transparency and moistened feeling to skin, lightening spots and making pores less noticeable, hair-growing effect in suppressing hair loss and promoting growth of hair, and an penetration accelerating effect in accelerating the penetration of preparations for external use, such as drugs, cosmetics or the like, into skin or the like.

The invention claimed is:
1. A composition consisting essentially of 0.01 to 3 wt% of carrageenan, one or more acid(s) selected from sulfuric acid, hydrochloric acid and nitric acid, and water, wherein said composition is in the form of viscous aqueous solution, gel or cream and the pH thereof is from 3.54 to 4.52.

2. The composition according to claim 1, wherein said composition is in the form of viscous aqueous solution and able to penetrate into the skin.

3. The composition according to claim 1, wherein said composition is able to increase transdermal absorption rate of physiologically active substances.

4. The composition according to claim 2, wherein said composition is able to increase transdermal absorption rate of physiologically active substances.

5. The composition according to claim 1, wherein the acid is sulfuric acid.

6. The composition according to claim 1, wherein the acid is hydrochloric acid.

7. The composition according to claim 1, wherein the acid is nitric acid.

* * * * *